US005543389A

United States Patent [19]
Yatvin et al.

[11] Patent Number: 5,543,389
[45] Date of Patent: *Aug. 6, 1996

[54] COVALENT POLAR LIPID-PEPTIDE CONJUGATES FOR USE IN SALVES

[75] Inventors: Milton B. Yatvin, Portland, Oreg.; Michael H B Stowell, Pasadena, Calif.

[73] Assignee: State of Oregon, Acting by and Through the Oregon State Board of Higher Education on Behalf of the Oregon Health Sciences University, a non profit organization, Portland, Oreg.

[*] Notice: The term of this patent shall not extend beyond the expiration date of Pat. No. 5,149,794.

[21] Appl. No.: 142,771

[22] Filed: Oct. 26, 1993

Related U.S. Application Data

[63] Continuation-in-part of Ser. No. 911,209, Jul. 9, 1992, Pat. No. 5,256,641, which is a continuation-in-part of Ser. No. 607,982, Nov. 1, 1990, Pat. No. 5,149,794.

[51] Int. Cl.⁶ .................. A61K 31/00; A61K 31/685
[52] U.S. Cl. .................. 514/2; 514/78; 514/863; 424/450; 536/51; 536/28.2; 530/300; 530/331; 530/329
[58] Field of Search .................. 536/29, 51; 514/28, 514/2, 863; 424/450; 538/300, 331, 329; 544/243, 153

[56] References Cited

PUBLICATIONS

Falk, et al., 1990, Nature 348:248–251.
Abbas, et al., 1991, Cellular and Mol. Immunol. (W. B. Saunders Co.; Philadelphia), pp. 116–136.
Faustman, et al., 1991, Science 254:1756–1771.
Hopp, 1984, Mol. Immunol. 21:13–16.
DeMagrialis, et al., 1992, Cell 68:625–634.
Lamont, et al., 1990, J. Immunol. 144:2493–2498.
Elliot, et al., 1990, Nature 348:195–197.
Parham, 1990, Nature 348: 647–675.
Sadegh–Nasseri & Germain, 1991, Nature 353:167–170.
Jardetzky, et al., 1991, Nature 353:326–329.
Lanzavecchia, et al., 1992, Nature 357:249–252.
Guéry, et al., 1992, J. Exp. Med. 175:1345–1352.
Wiesmüller, et al., 1991, Imm. 72:109–113.
Frisch, et al., 1991, Eur. J. Imm. 21:185–193.
Falk, et al., 1991, Nature 351:290–296.
Germain & Hendrix, 1991 Nature 353:134–139.

*Primary Examiner*—John W. Rollins
*Attorney, Agent, or Firm*—Banner & Allegretti, Ltd.

[57] ABSTRACT

This invention herein describes a method of facilitating the entry of drugs into cells at pharmokinetically useful levels and also a method of targeting drugs to specific organelles within the cell. This lipid/drug conjugate targeting invention embodies an advance over other drug targeting methods because through this method, intracellular drug concentrations may reach levels which are orders of magnitude higher than those achieved otherwise. Furthermore, it refines the drug delivery process by allowing therapeutic agents to be directed to certain intracellular structures. This technology is appropriate for use with antiproliferative drugs, in particular in combination with a multiplicity of other emolients and agents to make up topically-active substances such as salves, for rapid and efficient introduction of antiproliferative agents through the epidermis for treatment of skin diseases such as psoriasis.

36 Claims, 1 Drawing Sheet

COVALENT POLAR LIPID-PEPTIDE CONJUGATES FOR USE IN SALVES

This invention was made with government support under grants 1-R01-CA49416 and RR-00167 by the National Institutes of Health. The government has certain rights in the invention.

This application is a continuation-in-part of U.S. patent application Ser. No. 07/911,209, filed Jul. 9, 1992, now U.S. Pat. No. 5,256,641, issued Oct. 26, 1993, which was a continuation-in-part of U.S. patent application Ser. No. 07/607,982, filed Nov. 1, 1990, now U.S. Pat. No. 5,149,794, issued Sep. 22, 1992, each of which are herein incorporated by reference.

BACKGROUND OF THE INVENTION

1. Field of the Invention

A major goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. One common example of the need for such specificity is in the field of antiproliferative agent therapy, in which the amount of a variety of antiproliferative agents to be safely administered topically or locally to a patient is limited by their systemic cytotoxic effects.

In addition, it is recognized in the medical arts that certain subcellular organelles are the sites of pharmacological action of certain drugs or are involved in the biological response to certain stimuli. Specific delivery of diagnostic or therapeutic compounds to such intracellular organelles is thus desireable to increase the specificity and effectiveness of such clinical diagnostic or therapeutic techniques.

A. Drug Targeting

It is desirable to increase the efficiency and specificity of administration of a therapeutic agent to the cells of the relevant tissues in a variety of pathological states. This is particularly important as relates to antiproliferative agents. Such agents typically have pleiotropic antibiotic and cytotoxic effects that damage or destroy uninvolved cells and tissues as well as cells and tissues comprising the pathological site. Thus, an efficient delivery system which would enable the delivery of such drugs specifically to the diseased or affected tissues cells would increase the efficacy of treatment and reduce the associated "side effects" of such drug treatments, and also serve to reduce morbidity and mortality associated with clinical administration of such drugs.

Numerous methods for enhancing the cytotoxic activity and the specificity of drug action have been proposed. One method, receptor targeting, involves linking the therapeutic agent to a ligand which has an affinity for a receptor expressed on the desired target cell surface. Using this approach, a drug is intended to adhere to the target cell following formation of a ligand-receptor complex on the cell surface. Entry into the cell could then follow as the result of internalization of ligand-receptor complexes. Following internalization, the drug may then exert its therapeutic effects directly on the cell.

One limitation of the receptor targeting approach lies in the act that there are only a finite number of receptors on the surface of target cells. It has been estimated that the maximum number of receptors on a cell is approximately one million (Darnell et al., 1986, *Molecular Cell Biology*, 2d ed., W. H. Freeman: New York, 1990). This estimate predicts that there may be a maximum one million drug-conjugated ligand-receptor complexes on any given cell. Since not all of the ligand-receptor complexes may be internalized, and any given ligand-receptor system may express many-fold fewer receptors on a given cell surface, the efficacy of intracellular drug delivery using this approach is uncertain. Other known intracellular ligand-receptor complexes (such as the steroid hormone receptor) express as few as ten thousand hormone molecules per cell. Id. Thus, the ligand-receptor approach is plagued by a number of biological limitations.

Other methods of delivering therapeutic agents at concentrations higher than those achievable through the receptor targeting process include the use of lipid conjugates that have selective affinities for specific biological membranes. These methods have met with little success. (see, for example, Remy et al., 1962, J. Org. Chem. 27: 2491–2500; Mukhergee & Heidelberger, 1962, Cancer Res. 22: 815–22: Brewster et al., 1985, J. Pharm. Sci. 77: 981–985).

Liposomes have also been used to attempt cell targeting. Rahman et al., 1982, Life Sci. 31. 2061–71 found that liposomes which contained galactolipid as part of the lipid appeared to have a higher affinity for parenchymal cells than liposomes which lacked galactolipid. To date, however, efficient or specific drug delivery has not been predictably achieved using drug-encapsulted liposomes. There remains a need for the development of a cell- or organelle-targeting drug delivery system.

In response to the deficiencies encountered with receptor targeting, investigators have looked for other methods of delivering therapeutic agents at concentrations higher than those achievable through the receptor targeting process. Experiments suggested that lipids have selective affinities for specific biological membranes.

The selective association of certain lipids with specific biological membranes provided a possible avenue of drug targeting. In light of this possibility, researchers have attempted to target drugs by conjugating them with cholesterol. Unfortunately, these attempts have met with disappointing results (see, Remy et al., 1962, J. Org. Chem. 27:2491–2500; Mukhergee and Heidelberger, 1962, Cancer Res. 22: 815–22; Brewster et al., 19xx, J. Pharm. Sci. 77: 981–985, have had some success with carrying estradiol to the brain using pyridinium salts as carriers.

Another attempt at cell targeting through the use of lipids was made by Rahman et al., 1982, Life Sci. 31: 2061–71. These investigators found that liposomes which contained galactolipid as part of the lipid appeared to have a higher affinity for parenchymal cells than liposomes which lacked galactolipid. These researchers suggested that this finding might have utility in drug targeting.

An additional challenge in designing an appropriate drug delivery scheme is to include within the drug conjugate a functionality which could either accelerate or reduce the rate at which the drug is released upon arrival at the desired site. Such a functionality would be especially valuable if it allowed differential rates of drug release.

BRIEF SUMMARY OF THE INVENTION

The present invention is directed to an improved method for delivering biologically-active compounds to cells and cellular organelles in vivo and in vitro. This delivery system achieves such specific delivery of biologically-active compounds through conjugating the compounds with a polar lipid carrier. This invention has the specific advantage of facilitating the entry of such compounds into cells via the polar lipid carrier, achieving effective intracellular concentration of such compounds more efficiently and with more specificity than conventional delivery systems.

The invention provides compositions of matter comprising a biologically-active compound covalently linked to a polar lipid carrier molecule. Preferred embodiments also comprise a spacer molecule having two linker functional groups, wherein the spacer has a first end and a second end and wherein the polar lipid is attached to the first end of the spacer through a first linker functional group and the biologically-active compound is attached to the second end of the spacer through a second linker functional group. In preferred embodiments, the biologically-active compound is a drug, most preferably an antiproliferative drug or agent. Preferred polar lipids include but are not limited to sphingosine, ceramide, phosphatidyl oholine, phosphatidyl glycerol, phosphatidyl ethanolamine, phosphatidyl inositol, phosphatidyl serine, cardiolipin and phosphatidic acid.

The invention also provides compositions of matter comprising a biologically-active compound covalently linked to a polar lipid carrier molecule via a spacer molecule wherein the spacer allows the biologically-active compound to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the biologically-active compound at an intracellular site. Other embodiments of the spacer facilitate the enzymatic release of the biologically-active compound at an intracellular site.

In another embodiment of this aspect of the invention, the spacer molecule is a peptide of formula (amino acid)$_n$, wherein n is an integer between 2 and 25, preferably wherein the peptide comprises a polymer of a particular amino acid.

In other embodiments of the compositions of matter of the invention, the biologically-active compound of the invention has a first functional linker group, and a polar lipid carrier has a second functional linker group, and the compound is directly covalently linked to the polar lipid carrier by a chemical bond between the first and second functional linker groups. In preferred embodiments, each of the first and second functional linker groups is a hydroxyl group, a primary or secondary amino group, a phosphate group or substituted derivatives thereof or a carboxylic acid group.

In another aspect of the invention is provided compositions of matter comprising a drug covalently linked to a polar lipid carrier molecule. Preferred embodiments also comprise a spacer molecule having two linker functional groups, wherein the spacer has a first end and a second end and wherein the polar lipid is attached to the first end of the spacer through a first linker functional group and the drug is attached to the second end of the spacer through a second linker functional group. In preferred embodiments of the invention, the drug is an antiproliferative agent, most preferably methotrexate. Preferred polar lipids include but are not limited to sphingosine, ceramide, phosphatidyl choline, phosphatidyl glycerol, phosphatidyl ethanolamine, phosphatidyl inositol, phosphatidyl serine, cardiolipin and phosphatidic acid.

The invention also provides compositions of matter comprising an antiproliferative agent covalently linked to a polar lipid carrier molecule via a spacer molecule wherein the spacer allows the drug to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the antiproliferative drug at an intracellular site. Other embodiments of the spacer facilitate the enzymatic release of the antiproliferative drugs of the invention at an intracellular site.

In still further embodiments of the compositions of matter of the invention, the antiviral or antineoplastic drug of the invention has a first functional linker group, and a polar lipid carrier has a second functional linker group, and the drug is directly covalently linked to the polar lipid carrier by a chemical bond between the first and second functional linker groups. In preferred embodiments, each of the first and second functional linker groups is a hydroxyl group, a primary or secondary amino group, a phosphate group or substituted derivatives thereof or a carboxylic acid group.

In another embodiment of this aspect of the invention, the spacer molecule is a peptide of formula (amino acid)$_n$, wherein n is an integer between 2 and 25, preferably wherein the peptide comprises a polymer of a particular amino acid.

A preferred embodiment of this aspect of the invention includes compositions of matter that are N-methotrexate ceremide.

Particular preferred embodiments are salves and other topically or locally applied compositions comprising the drug/polar lipid conjugates of the invention and any of a variety of emolients or other commonly encountered components of cremes, salves, poultices, lotions, gels or other substances well-known in the art for applying compounds to skin and other tissues. Appropriate formulations of such compositions comprising the drug/polar lipid conjugates of the invention will be apparent and within the skill of one of ordinary skill in this art to advantageously prepare in view of the instant disclosure.

As disclosed herein, the invention comprehends a lipid-drug conjugate wherein the lipid will selectively associate with certain biological membranes, and thereby facilitate entry of the drug into cells and cellular organelles. The spacer component of the conjugates of the invention will preferably act to release the drug from the lipid, target the conjugate to the cell, or perform other functions to maximize the effectiveness of the drug.

This type of conjugate has numerous advantages. First, the drug-polar lipid conjugates of the invention will promote the intracellular entry of a variety of potentially useful drugs at pharmokinetical rates not currently attainable. Second, the range of targeted cell types is not limited per se by particular, limited biological properties of the cell such as the number and type of specific receptor molecules expressed on the cell surface, as are receptor-specific drug targeting methods. Third, in contrast to traditional attempts to simply target drugs to specific cells, this method may target drugs to specific intracellular organelles and other intracellular compartments. Fourth, the compositions of matter of the invention incorporate a variable spacer region that may allow pharmacologically-relevant rates of drug release from polar lipid carrier molecules to be engineered into the compositions of the invention, thereby increasing their clinical efficacy and usefulness. Thus, time-dependent drug release and specific drug release in cells expressing the appropriate degradative enzymes are a unique possibility using the drug-lipid conjugates of the invention. Finally, the conjugates of the invention can be combined with other drug delivery approaches to further increase specificity and to take advantage of useful advances in the art.

Specific preferred embodiments of the present invention will become evident from the following more detailed description of certain preferred embodiments and the claims.

DETAILED DESCRIPTION OF THE PREFERRED EMBODIMENTS

Figure 1:
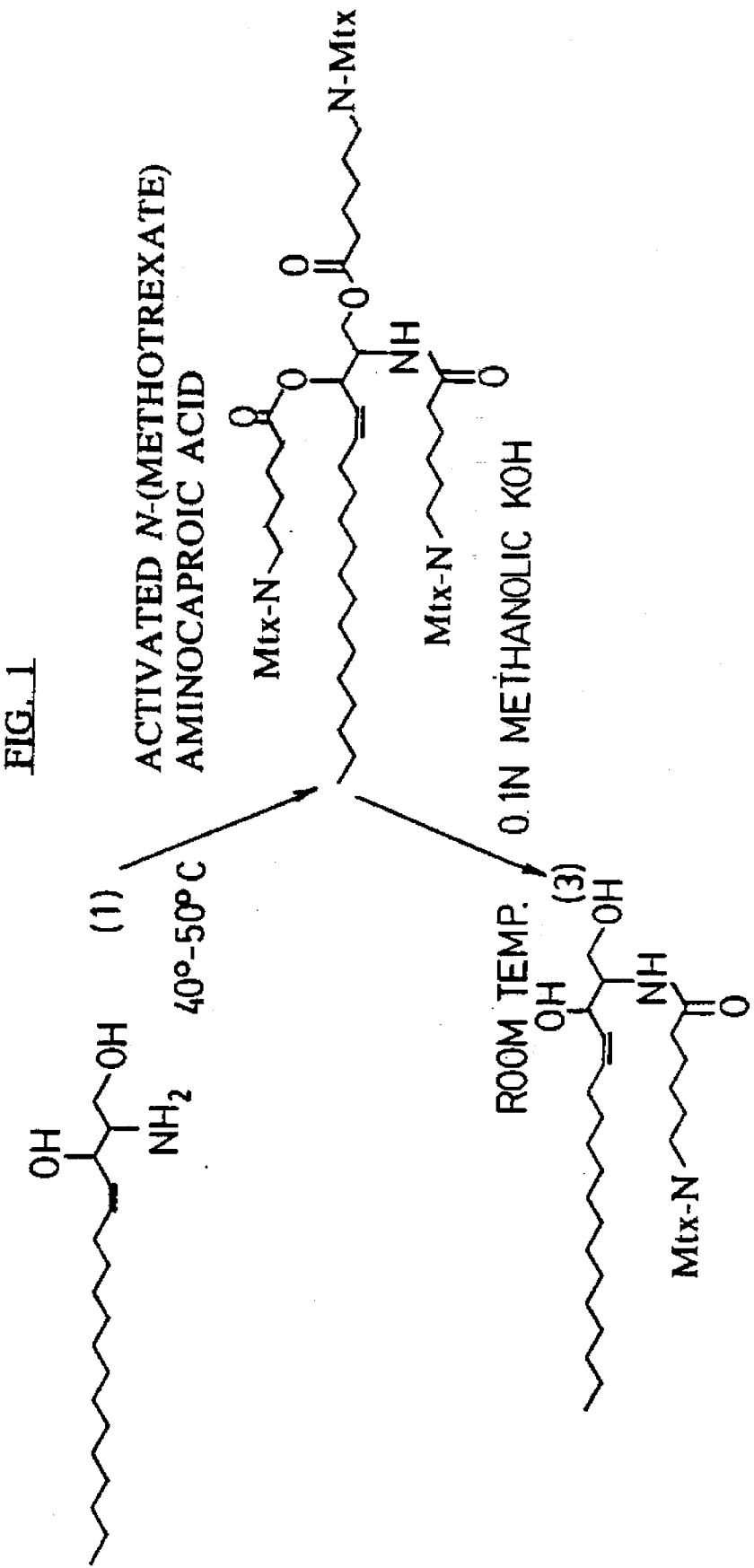
FIG. 1 depicts the synthetic scheme put forth in Example 1.

The present invention provides compositions of matter and methods for facilitating the entry into cells of biologically-active compounds. For the purposes of this invention, the term "biologically-active compound" is intended to encompass all naturally-occurring or synthetic compounds capable of eliciting a biological response or having an effect, either beneficial or cytotoxic, on biological systems, particularly cells and cellular organelles. These compounds are intended to include but are not limited to all varieties of drugs, particularly antiproliferative drugs and agents.

The compositions of matter provided by the invention comprise the biologically-active compounds of the invention covalently linked to a polar lipid carrier. A polar lipid carrier, as defined herein is intended to mean any polar lipid having an affinity for, or capable of crossing, a biological membrane, including but not limited to sphingosine, ceramide, phosphatidyl choline, phosphatidyl glycerol, phosphatidyl ethanolamine, phosphatidyl inositol, phosphatidyl serine, cardiolipin, phosphatidic acid, sphingomyelin and other sphingolipids, as these terms are understood in the art (see, Lehninger, Biochemistry, 2d ed., Chapters 11 & 24, Worth Publishers: New York, 1975).

The compositions of matter of the invention may be further comprised of a spacer moiety comprising a first end and a second end, each end of the spacer having a functional linking group. For the purposes of this invention, the term "spacer" or "spacer moiety" is intended to encompass any chemical entity that links the biologically-active compound and the polar lipid. Such spacer moieties may be designed to facilitate the attachment of the conjugates of the invention to a target cell, or to facilitate, influence, modulate or regulate the release of the biologically-active compound at the desired target site. Such spacers may also facilitate enzymatic release at certain intracellular sites. Spacer groups, as described herein, include, but are not limited to aminohexanoic acid, polyglycine, polyamides, polyethylenes, and short functionalized polymers having a carbon backbone which is from one to about twelve carbon molecules in length. Particularly preferred embodiments of such spacer moieties comprise peptides of formula (amino acid)$_n$, wherein n is an integer between 2 and 25 and the peptide is a polymer of a particular amino acid.

The term "linker functional group" is defined herein as any functional group for covalently binding the polar lipid carrier or biologically-active agent to the spacer group. These groups can be designated either "weak" or "strong" based on the stability of the covalent bond which the linker functional group will form between the spacer and either the polar lipid carrier or the biologically-active compound. The weak functionalities include, but are not limited to phosphoramide, phosphoester, carbonate, amide, carboxyl-phosphoryl anhydride, ester and thioester. The strong functionalities include, but are not limited to ether, thioether, amine, amide and ester. The use of a strong linker functional group between the spacer group and the biologically-active compound will tend to decrease the rate at which the compound will be released at the target site, whereas the use of a weak linker functional group between the spacer group and the compound may act to facilitate release of the compound at the target site. Enzymatic release is, of course, also possible, but such enzyme-mediated modes of release will not necessarily be correlated with bond strength in such embodiments of the invention. Spacer moieties comprising enzyme active site recognition groups, such as spacer groups comprising peptides having proteolytic cleavage sites therein, are envisioned as being within the scope of the present invention.

The present invention provides methods and compositions of matter for facilitating the entry of antiproliferative agents, drugs and compounds into dermal and epidermal cells and across mucosal membranes where appropriate, for efficient delivery of such compounds locally and topically for the treatment of animal, preferably human, diseases and pathological conditions, such as psoriasis.

The invention specifically provides methods for preparing and administering such antiproliferative compounds for use in treating pathological conditions in vivo.

Animals to be treated with polar lipid-antiproliferative agent conjugates using the methods of the invention are intended to include all vertebrate animals, preferrably domesticated animals, such as cattle, horses, goats, sheep, fowl, fish, household pets, and others, as well as wild animals, and most preferably humans.

The following Examples illustrate certain aspects of the above-described method and advantageous results. The following examples are shown by way of illustration and not by way of limitation.

EXAMPLE 1

An antiproliferative agent is prepared wherein the antiproliferative drug methotrexate (Mtx) is conjugated to sphingosine via a 6-aminocaproic acid spacer. This reaction scheme is illustrated in FIG. 1. The primary amino and hydroxyl groups of sphingosine are acylated by reaction with activated N-(methotrexate)aminocaproic acid overnight at 40°–50° C., followed by base hydrolysis in 0.1N methanolic KOH. The Mtx derivative of 6-aminocaproic acid is synthesized by activating the carboxylic acid moiety of Mtx and reacting with 6-aminocaproic acid for 2 days at 60°–70° C. This reaction is stopped under acidic conditions to liberate anhydrides that form under these conditions.

It should be understood that the foregoing disclosure emphasizes certain specific embodiments of the invention and that all modifications or alternatives equivalent thereto are within the spirit and scope of the invention as set forth in the appended claims.

What is claimed is:

1. A composition of matter comprising an antiproliferative drug, a polar lipid carrier, two linker functional groups and a spacer, wherein the spacer has a first end and a second end and wherein the polar lipid is attached to the first end of the spacer through a first linker functional group and the antiproliferative drug is attached to the second end of the spacer through a second linker functional group.

2. The composition of matter of claim 1 wherein the drug is methotrexate.

3. A composition of matter according to claim 1 wherein the spacer allows the antiproliferative drug to act without being released at an intracellular site and wherein the first linker functional group attached to the first end of the spacer is strong and the second linker functional group attached to the second end of the spacer is weak.

4. A composition of matter according to claim 3 that is methotrexateglycylglycylglycylgylcyl ceramide ester.

5. A composition comprising the composition of matter of claim 4 and a medicinal ointment or salve.

6. A composition of matter according to claim 3 that is methotrexateglycylglycylglycylgylcyl ceramide ester.

7. A composition comprising the composition of matter of claim 6 and a medicinal ointment or salve.

8. A composition of matter according to claim 3 that is methotrexatevalinylvalinyl sphingosine amide.

9. A composition comprising the composition of matter of claim 8 and a medicinal ointment or salve.

10. A composition of matter according to claim 1 wherein the spacer allows the facilitated hydrolytic release of the antiproliferative drug at an intracellular site and wherein the first linker functional group attached to the first end of the spacer is strong and the second linker functional group attached to the second end of the spacer is weak.

11. A composition of matter according to claim 1 wherein the spacer allows the facilitated enzymatic release of the antiproliferative drug at an intracellular site and wherein the first linker functional group attached to the first end of the spacer is strong and the second linker functional group attached to the second end of the spacer is weak.

12. A composition of matter according to claim 1 wherein the polar lipid is sphingosine, ceramide, phosphatidyl choline, phosphatidyl glycerol, phosphatidyl ethanolamine, phosphatidyl inositol, phosphatidyl serine, cardiolipin or phosphatidic acid.

13. A composition of matter according to claim 1 wherein the spacer is a peptide of formula (amino acid)$_n$, wherein n is an integer between 2 and 25, and the peptide comprises a polymer of a particular amino acid.

14. A composition of matter according to claim 1 that is methotrexate-[tri-β-hydroxypropionylester]-O$^x$-ceramide ester.

15. A composition comprising the composition of matter of claim 14 and a medicinal ointment or salve.

16. A composition of matter according to claim 1 that is methotrexateaminohexanoyl sphingosine amide.

17. A composition comprising the composition of matter of claim 16 and a medicinal ointment or salve.

18. A composition comprising the composition of matter of claim 1 and a medicinal ointment or salve.

19. A composition of matter comprising an antiproliferative drug having a first functional linker group, and a polar lipid carrier having a second functional linker group, wherein the drug is covalently linked to the polar lipid carrier by a chemical bond between the first and second functional linker groups.

20. A composition of matter according to claim 19 wherein the first functional linker group is a hydroxyl group, a primary or secondary amino group, a phosphate group or substituted derivatives thereof or a carboxylic acid group.

21. A composition of matter according to claim 19 wherein the second functional linker group is a hydroxyl group, a primary or secondary amino group, a phosphate group or substituted derivatives thereof or a carboxylic acid group.

22. A composition of matter according to claim 19 wherein the polar lipid is sphingosine, ceramide, phosphatidyl choline, phosphatidyl glycerol, phosphatidyl ethanolamine, phosphatidyl inositol, phosphatidyl serine, cardiolipin or phosphatidic acid.

23. The composition of matter of claim 19 wherein the drug is methotrexate.

24. A composition of matter according to claim 19 that is methotrexate-O$^x$-ceramide ester.

25. A composition comprising the composition of matter of claim 24 and a medicinal ointment or salve.

26. A composition of matter according to claim 19 that is N-methotrexate ceramide.

27. A composition comprising the composition of matter of claim 26 and a medicinal ointment or salve.

28. A composition comprising the composition of matter of claim 19 and a medicinal ointment or salve.

29. A method of treating a pathological condition or disease state in in skin of an animal, wherein the pathological condition or disease state results from an abnormal proliferation of cells in the animal, comprising the step of administering to the animal the composition of matter of claim 1 in an acceptable carrier or formulation and in an amount sufficient to alleviate the pathological condition or disease state in the animal.

30. The method of claim 29 wherein the animal is a human.

31. The method of claim 29 wherein the disease is psoriasis.

32. A method according to claim 29, wherein the antiproliferative drug-polar lipid conjugate is formulated as a medicinal ointment or salve.

33. A method of treating a pathological condition or disease state in in skin of an animal, wherein the pathological condition or disease state results from an abnormal proliferation of cells in the animal, comprising the step of administering to the animal the composition of matter of claim 19 in an acceptable carrier or formulation and in an amount sufficient to alleviate the pathological condition or disease state in the animal.

34. The method of claim 33 wherein the animal is a human.

35. The method of claim 33 wherein the disease is psoriasis.

36. A method according to claim 33, wherein the antiproliferative drug-polar lipid conjugate is formulated as a medicinal ointment or salve.

* * * * *

UNITED STATES PATENT AND TRADEMARK OFFICE
CERTIFICATE OF CORRECTION

PATENT NO. : 5,543,389
DATED : August 6, 1996
INVENTOR(S) : Milton B. Yatvin and Michael H B Stowell It is certified that error appears in the above-indentified patent and that said Letters Patent is hereby corrected as shown below:

On the title page: Item [54] and Column 1, line 1 &2

Please delete the title of the invention and substitute the following title:

--Covalent Polar Lipid-Antiproliferative Drug Conjugates for Use in Salves--

Signed and Sealed this

Seventh Day of January, 1997

*Attest:*

BRUCE LEHMAN

*Attesting Officer*  *Commissioner of Patents and Trademarks*